(12) United States Patent
Howse

(10) Patent No.: US 6,344,208 B1
(45) Date of Patent: Feb. 5, 2002

(54) PHEROMONE BAITS FOR SOCIAL INSECTS

(76) Inventor: Philip Edwin Howse, Gosport (GB)

( * ) Notice: Subject to any disclaimer, the term of this patent is extended or adjusted under 35 U.S.C. 154(b) by 0 days.

(21) Appl. No.: 08/099,248

(22) Filed: Jul. 29, 1993

Related U.S. Application Data

(63) Continuation of application No. 07/776,262, filed as application No. PCT/GB90/00415 on Mar. 19, 1990, now abandoned.

(30) Foreign Application Priority Data

Mar. 20, 1989 (GB) .............................................. 8906382
Mar. 19, 1990 (WO) .............................. PCT/GB90/00415

(51) Int. Cl.[7] .............................................. A01N 25/10
(52) U.S. Cl. .................. 424/405; 424/84; 424/409; 424/410; 424/DIG. 10; 424/DIG. 11; 514/558; 514/644; 514/646; 514/675; 514/724; 514/739; 514/755; 514/763
(58) Field of Search .................. 424/405, 84, DIG. 10, 424/DIG. 11, 410, 409, 407, 408; 514/558, 644–646, 675, 690, 724, 729, 738, 739, 755, 762, 763

(56) References Cited

FOREIGN PATENT DOCUMENTS

GB 2018593 * 10/1979 .................. 424/408

OTHER PUBLICATIONS

Kydonieus, et, al. editors, Insect Suppression with Controlled Release Pheromone Systems vol. I, 1982 CRC press.*

Stoner et al. Toxicity effects in Honey bees–p. 212, chem. abstract #191146e vol. 103, 1985.*

Morgan et al. Mandibular gland secredon of the ant myrmica scabrinodis chem. abstract #143599A vol. 89, 1978 p. 338.*

* cited by examiner

*Primary Examiner*—Neil S. Levy
(74) *Attorney, Agent, or Firm*—Kilpatrick Stockton LLP

(57) ABSTRACT

An insecticidal system for killing social insects comprises an insecticide together with a synthetic equivalent, such as 3-octanol, to at least one component of the alarm pheromone of the insect. The system is particularly effective against members of the Acromyrmex, Atta and Solenopsis species.

12 Claims, 6 Drawing Sheets

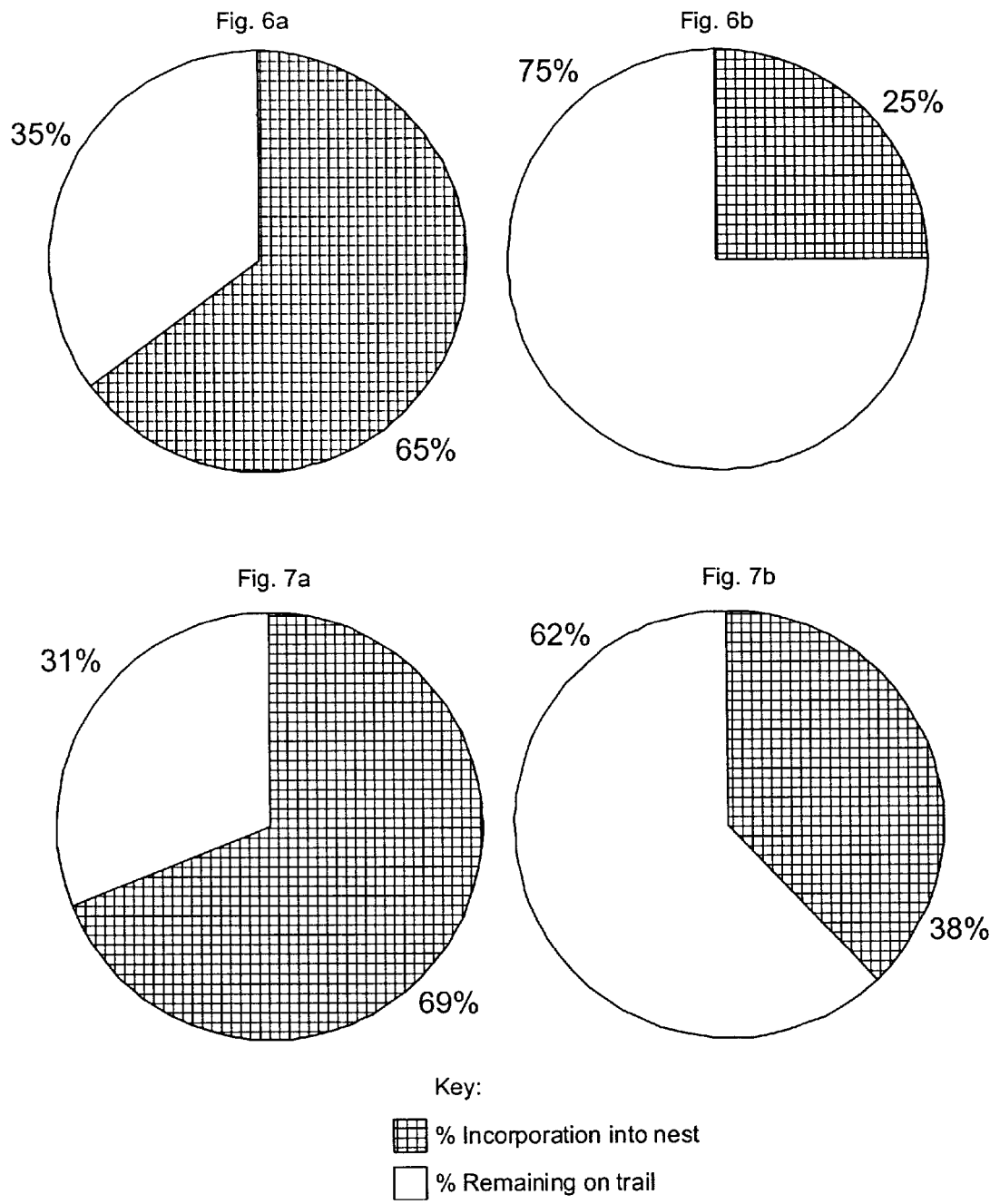

PHEROMONE BAITS FOR SOCIAL INSECTS

CROSS-REFERENCE TO RELATED APPLICATIONS

This application is a continuation of U.S. application Ser. No. 07/776,262 filed Nov. 18, 1991, now abandoned, which is the National Stage of PCT/GB90/00415, filed Mar. 19, 1990.

Social insects, examples of which are ants, bees, wasps and termites, communicate using pheromones which are chemical messengers acting between members of the same species. Threat or danger to the colony is communicated by volatile alarm pheromones.

Research carried out on social insects has shown that alarm pheromones are generally a complex mixture of the chemical compounds. Such a mixture will usually alert, alarm and attract nestmates to the release site, where they attack any intruder. In some species, there is evidence that different compounds within a mixture affect selected aspects of behaviour, such as orientation towards the source or biting.

In some areas the leaf-cutting ant is a particular pest. Control of these pests is carried out with the use of a bait comprised of a carrier (often dried citrus pulp) impregnated with a toxicant, for example Mirex (trade mark), enclosed in a plastic sachet for protection against rain and decomposition. Mirex (TM) is an ant bait with Dodecachlorooctahydro-1,3,4 metheno-2H-cyclobuta (cd) pentalene as its active ingredient. The insecticide is formulated in granules of material of vegetable origin such as dried citrus pulp. The sachets are distributed on the ground in areas where the ants are active. When cut open by the ants the contents are taken to the nest as a food source and the toxicant is spread around the colony, usually causing its death. Such baits whether initially protected in plastic envelopes or not must be discovered and exploited very quickly by the ants or they will decompose rapidly in a humid tropical environment. Therefore, anything which increases the attractiveness of the bait and improve pick-up rate would be extremely useful.

Other social insects to which are particular pests include members of the Atta genus, such as Atta sexdens, Atta laevigata and Atta bisphaerica, which are also leaf cutting ants, and members of the Solenopsis genus, fire ants.

The invention provides an insecticidal system for social insects comprising a means for killing the insects together with synthetic equivalent to at least one component of the alarm pheromone of the insect.

In a preferred embodiment the insecticidal system is a composition comprising a synthetic equivalent to at least one component of the alarm pheromone of the insect, together with an insecticide for the insect.

Once the insects have been attracted to the bait, they may be killed either in situ by, for example, being killed in a trap and retained therein or exposed to insecticides therein, or by being provided with a slow-acting toxicant which they take to their nest, where it kills large numbers of insects.

Leaf cutting ants live in symbiosis with a fungus which breaks down plant material into a form assimilable by the ants. Incorporation of a fungicide, such as pentachloronitrobenzene or Benomyl, for this fungus in a system according to the invention will result in the death of the fungus and so the nest.

The invention also provides a method of controlling social insects comprising using a synthetic equivalents to at least one component of the alarm pheromone of the insect to attract the insect to an insecticide for the insect or to another means of killing the insect. The composition is placed suitably close to the nests of the insects.

Recent research by the applicant on the neotropical leaf-cutting ant Acromyrmex octospinosus has shown that t components of the alarm pheromone of this ant, namely 3-octanol and 3-octanone, attract nestmates and induce the laying of trails around the source which ensure that nestmates are then attracted towards the source for some time and attack the source on arrival. It appears that 3-octanone mainly causes recruitment of ants from the peripheral area, while 3-octanol mainly controls attraction to the source, the laying of pheromone trails radiating out from the source, and biting.

The natural alarm pheromone of the ants is unsuitable for use as a bait for subsequent incorporation in the nest. The concept of alarm pheromones in general implies that they are totally inappropriate substances for use in food baits as such baits would then be treated as aliens or enemies and attacked and removed.

It has now been found in laboratory trials that if 3-octanol and 3-octanone are synthesised, the synthetic chemicals will prolong the sequence of alerting, marking with trail substances around the source, biting and recruitment of nestmates from the peripheral area, especially when both chemicals are used together. This is significantly different from the behaviour induced by release of the natural pheromone from crushed workers, in which the above sequence is very shortlived, terminating in arrestance of nestmates at the source for long periods without attack and with subsequent removal of the body to rubbish dumps outside the nest. It is expected that this surprising effect will be shown by synthetic components of pheromones of other insects, especially social insects.

The sequence of behaviour induced in the ant by the two synthetic compounds (which do not represent the totality of compounds in the natural secretion) is a magnified and prolonged section of the natural sequence of behaviour induced by the naturally produced pheromone. The synthetic pheromone compounds may therefore be used in food baits in contrast to what would be expected.

Similar behaviour can be induced in other insect species, such as Atta, including A. sexdens, A. laevigata and A. bisphaerica, and Solenopsis (fire ants) by use synthetic alarm pheromone components. Synthetic alarm pheromone components which are useful also include nonanol, decanal dodecanal, 2-phenylethanol, citral, farnesol, 6-methyl-5-hepten-2-one, 4-methyl-3-heptanone, decanoic acid, geraniol, tetradecanal or β-pinene.

The invention will be further described, by way of example, with reference to the drawings in which FIG. 1 shows a rubber bung for slow-release of synthetic pheromone components;

FIGS. 6a and 6b are graphs showing the results of Trial 3;

FIGS. 7a and 7b are graphs showing the results of Trial 4; and

TRIALS

Figure 1:
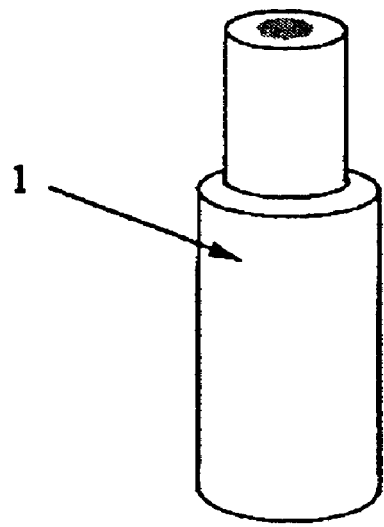
Figure 2:
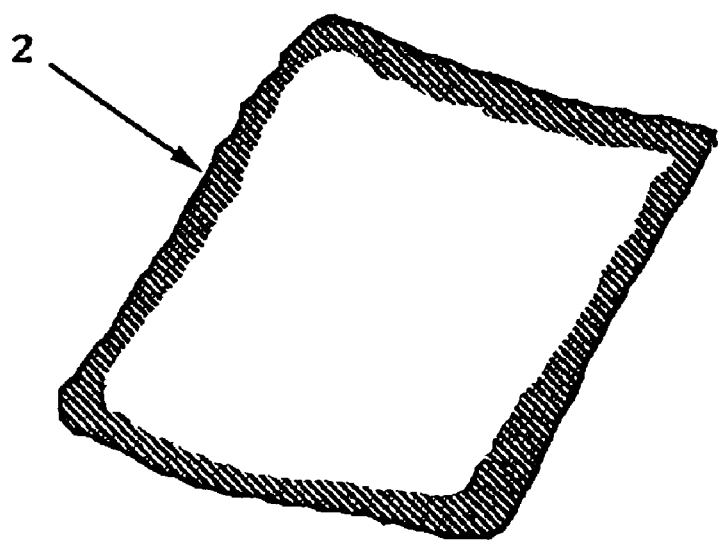
FIG. 2 shows a sachet into which the bung of FIG. 1 may be inserted.
Figure 3:
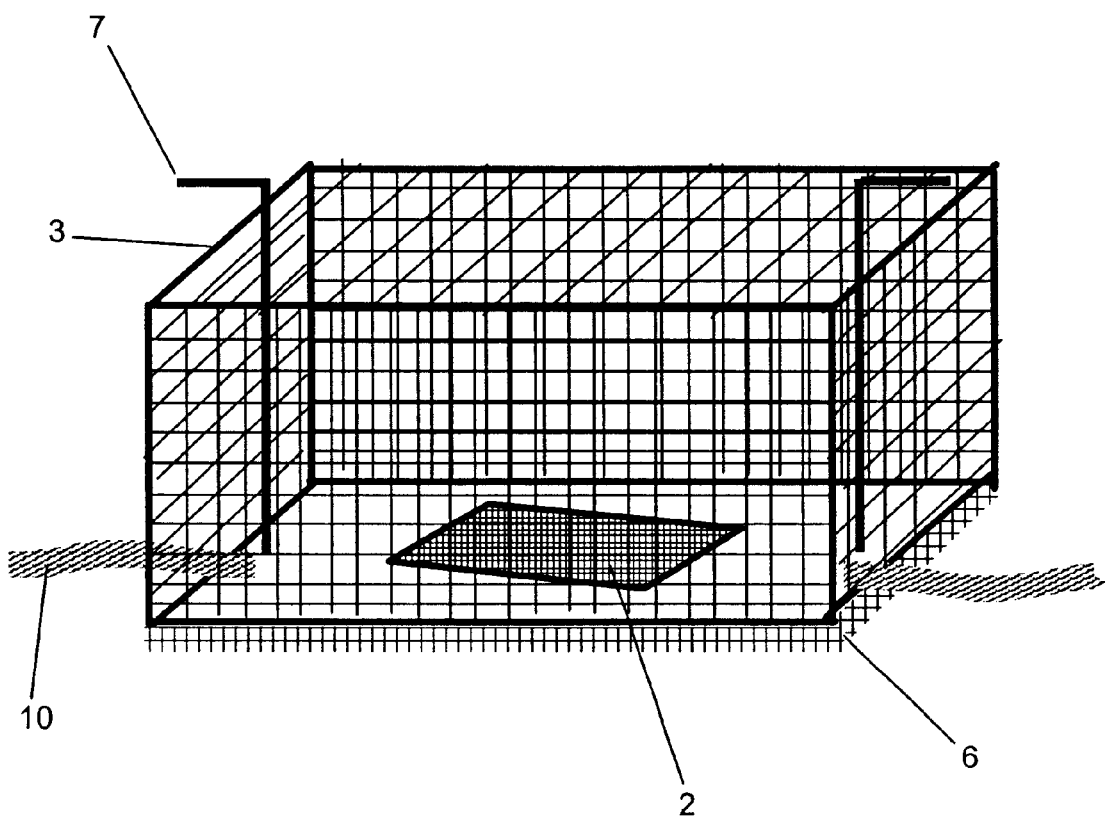
FIG. 3 shows a wire cage for holding the sachet of FIG. 2.

Field trials were carried out on *Acromyrmex octospinosus* and *Atta sexdens*.

*Acromyrmex octospinosus* Four different treatments were prepared:

Treatment a) 10 µl synthetic pheromone component 3-octanol

Treatment b) 10 µl synthetic pheromone component 3-octanone

Treatment c) 10 µl synthetic pheromone component 3-octanol+10 µl synthetic pheromone component 3-octanone (total 20 µl)

Treatment d) control (no pheromone component)

The two synthetic alarm pheromone components were micropipetted onto the surface of rubber bungs 1 which were then left to absorb the synthetic pheromone components and dry. This provides the synthetic pheromone components in slow-release formulation. The control experiments employed clean rubber bungs. The sachets 2 are each made from two approximately 8 $cm^2$ squares of black polythene, heat sealed on three sides. The sachets were filled with 5 grams of Mirex 250 (TM) in pellet form and the fourth side was sealed. The cages 3, which have wooden floors 6, were positioned on active ant trails 10 and secured to the ground with two metal pegs 7 in such a way that the ants were forced to re-establish the trail 10 across the floor of the cage. In the trials, each cage was positioned on the trail of a different nest at least 24 hours prior to the start of the trial, allowing ample time for the trail to re-establish itself.

The first trial (Trial 1) employed sachets which were sealed immediately after filling with Mirex 250 (TM). The bungs and sachets were taken to the field site. A small slit was made in the sachet and a bung was then inserted. One sachet and bung was placed in each cage, with the slit in the sachet facing downwards.

In the second trial (Trial 2) the pheromone bung was sealed inside the sachet containing Mirex 250 (TM) in the laboratory. The sealed sachets were transported to the field site and placed inside the cages.

In both trials the treatments were randomly allocated to the cages according to a computer generated random number sequence.

Figure 4:
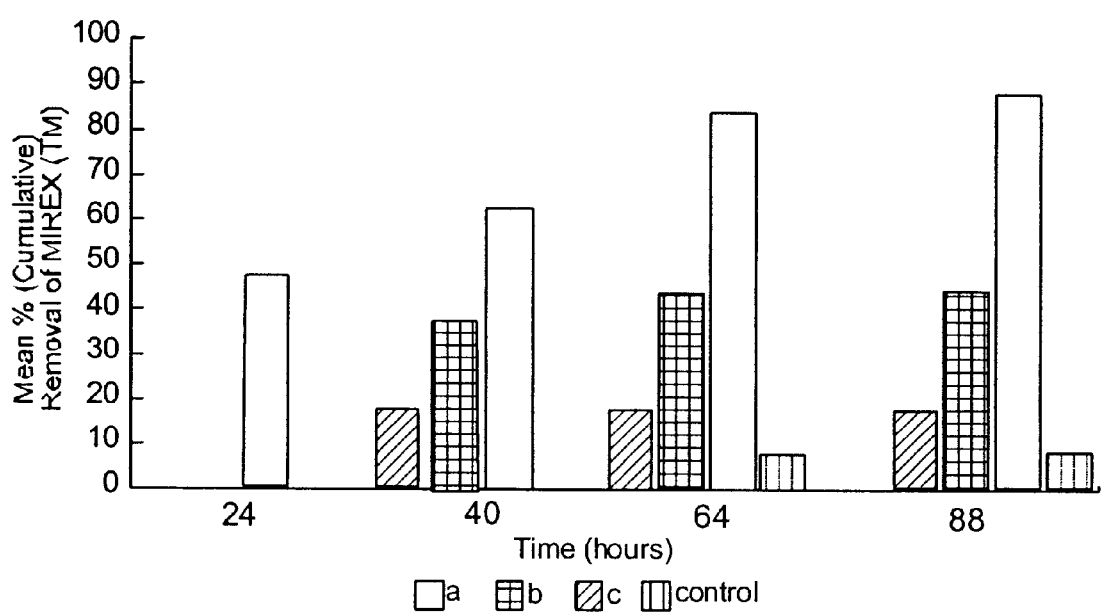
FIG. 4 is a graph showing the results of trial 1.
Figure 5:
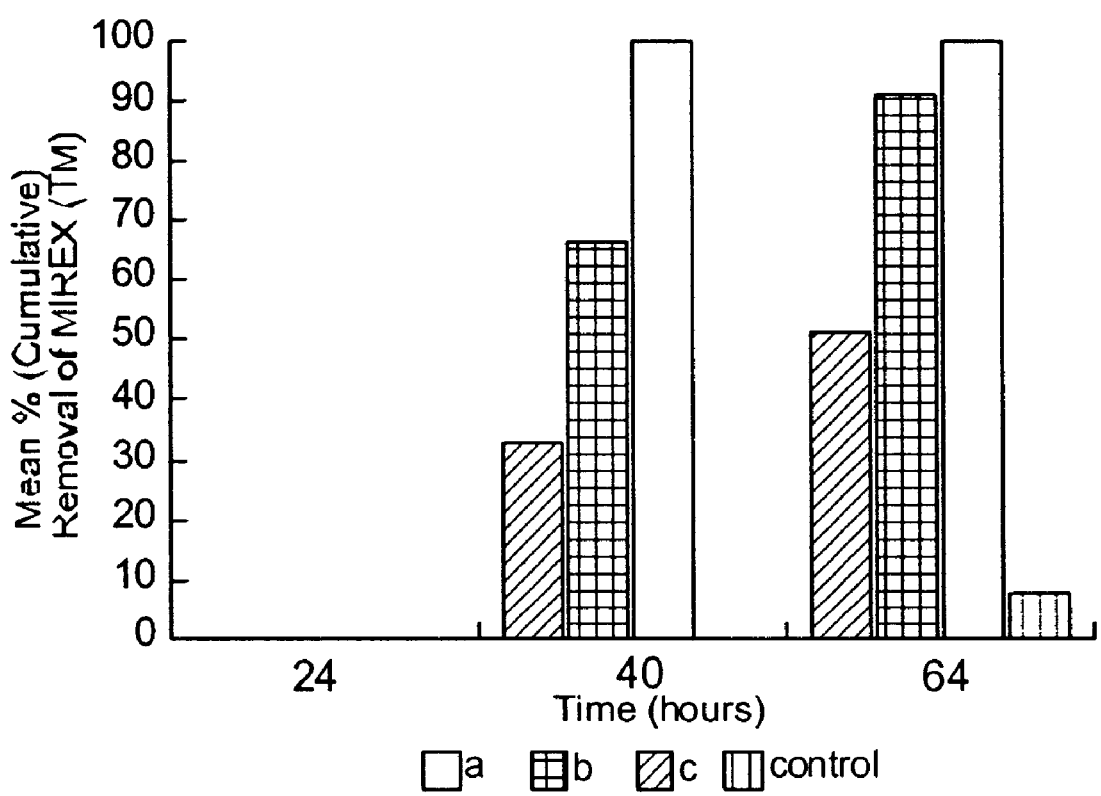
FIG. 5 is a graph showing the results of trial 2.

Comparison with the controls (no pheromone) showed that baits containing synthetic pheromone component were discovered and exploited much more rapidly than standard control baits without synthetic pheromone component (see FIGS. 4 and 5). This result is particularly marked when the two synthetic pheromone components are used together. In the field the synthetic pheromone component attracts the ants, induces recruitment by the first ants to arrive, stimulates biting and cutting open of the plastic sachet, and then, unexpectedly, transport of the total contents back to the nest, where the insecticide kills the insects. Control of this species by baiting can thus be greatly enhanced in efficiency with the incorporation of synthetic alarm pheromone components, especially 3-octanol and 3-octanone.

*Atta sexdens:*

The insecticide bait Mirex was used in all the trials. In Trials 3 and 4 the bait was presented to the ants in black plastic sachets 8 $cm^2$ placed inside wire cages, which provided protection from cattle, horses, small manamals and birds. The empty cages were placed in the field 24 hours prior to the start of the experiment. The Mire sachets were prepared and a component of mandibular gland alarm pheromone of the ant species concerned was added to the treatment sachets. In Trial 5 the sachets were not placed in cages but were scattered randomly at the cutting site. Five components or the alarm pheromone were tested. Rubber septa, used to provide a slow-release substrate, were dosed with 50 µl of component and then sealed inside the Mirex sachets. Control sachets were sealed with untreated rubber septa. The sachets were transferred immediately to the field sites. The fate of the sachets was then monitored over a 3 day period.

In a preliminary trial, sachets were placed directly on the mounds of Atta sexdens. These attracted very few ants, and in subsequent trials sachets were placed on foraging trials or in areas where the ants were cutting vegetation.

Trial 3: Sachets were placed 1 metre from the nest entrance hole on active trials of *A. sexdens*. Five synthetic components of the alarm pheromone were tested, separately; citral, farnesol, 6-methyl-5-hepten-2-one, 4-methyl-3-heptanone and geraniol. All test sachets were cut open and the contents transported into the nest. The results for the five synthetic pheromones were pooled. FIG. 6a shows the rate of removal after 12$h$ compared with controls shown in FIG. 6b.

Trial 4: This trial was conducted as for Trial 3, but using the component mixture with 20 µl of each component and a 2-component mixture of citral and 4-methyl-3-heptanone, with 50 µl of each component were compared with controls. The results were again pooled. FIG. 7a shows the averaged removal rates after 16$h$, compared with controls shown in FIG. 7b.

Trial 5: Sachets containing, separately, citral (E), 4-methyl-3-heptanone H and 6-methyl-5-hepten-2-one (G) were distributed randomly over an area of about 10 $m^2$ where ants were actively cutting leaves. Sachets with pheromone components were discovered and opened immediately, and with 4-methyl-3-heptanone all the bait had been transported back to the nest within 30 minutes, as can be seen from FIG. 8.

Figure 8:
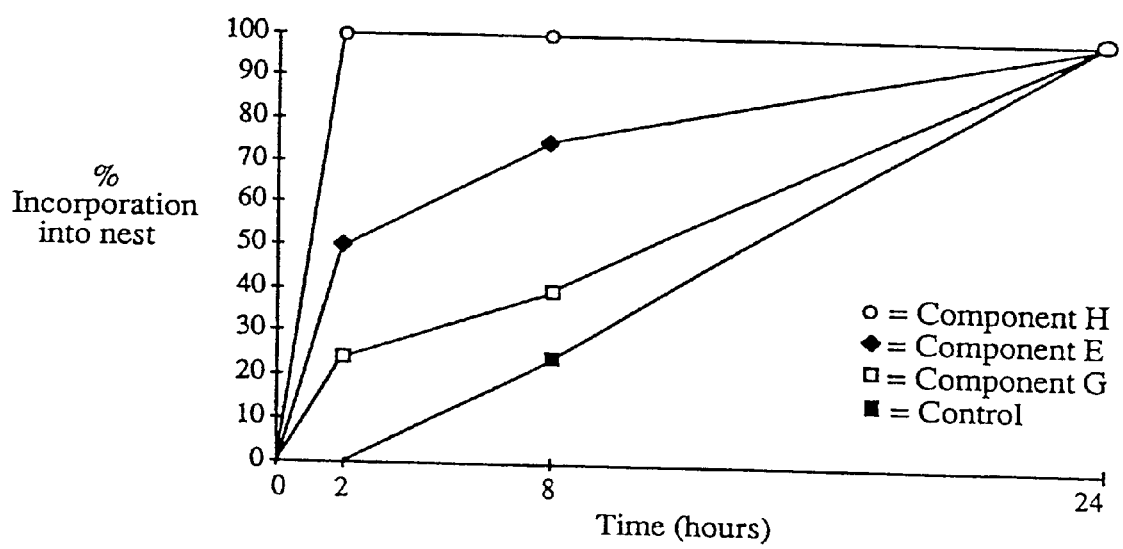
FIG. 8 is a graph showing the result of Trial 5.

These results confirm that the principle demonstrated in field tests with Acromyrmex applies also to Atta species. Certain alarm pheromone components attract foraging workers at a distance, decreasing discovery times compared with conventional baits, stimulate pickup and transport of bait particles to the nest without any rejection occurring en route. Thus the rate of incorporation of toxic bait into a nest can be around 10 times faster when the bait is presented with alarm pheromone components (FIG. 8). The faster the bait is harvested after exposure the less likely it is to be made ineffective by rain or microbial biodegradation, which occurs very rapidly in tropical conditions. It is also less likely to be picked up by other animals.

In order to confirm the efficacy of systems of the invention against *A. laevigata* and *A. bisphaerica*, sachets containing about 50 µl of solvent extracts of the insect heads on a rubber septum were placed on active foraging trails. All bait was transported back to the nest in 2 h in the case of *A. laevigata* and 4 h in the case of *A. bisphaerica*. This implies that use of a system of the invention with these insects will be effective.

Instead of insecticides, other means of killing insects can be employed. The synthetic pheromone components may be used to lure the insects to traps, such as a sticky surface or an electric grid. An electric grid trap, as described in WO 80/1748, has a surface accessible to insects which changes its position, in response to an electrical signal, so as to dislodge the insect into a trapping area. The trapping area contains a sticky surface to retain the insects until they are dead. This method may be particularly useful for insects such as wasps and bees.

Analogous systems of alarm communication are known to exist in most of it not all social insect species. Selected components of natural alarm pheromone may therefore be used in a similar way in baiting using insecticide, or other control method such as traps. In particular the method would be useful against other species of leaf cutting ants, for example other members of the Acromyrmex and *Atta* genera, which are major economic pests in the Americas and fire ants (Solenopsis species) which are again major pests in the U.S.A. and countries to the south.

What is claimed is:

1. A method of controlling a population of leaf-cutter ants by inducing foraging members of said population of leaf-cutter ants to transport a fungicide back to their nest due to the behavior-modifying effects of a behavior-modifying substance on said foraging leaf-cutter ants such that said fungicide is distributed to other members of said population of leaf-cutter ants and said leaf-cutter ants are killed as a result of exposure to said fungicide, said method comprising the steps of:

providing to said foraging leaf-cutter ants a bait comprising:
  (1) a fungicide selected from the group consisting of pentachloronitrobenzene and Benomyl;
  (2) a carrier for said fungicide which is transportable by said foraging leaf-cutter ants from a location external to said leaf-cutter ants' nestback to said population of leaf-cutter ants; and
  (3) a behavior-modifying substance for said foraging leaf-cutter ants comprising a mixture of 3-octanol and 3-octanone, said behavior-modifying substance being in association with said fungicide.

2. A method of controlling a population of ants by inducing foraging members of said population of ants to transport an insecticide back to their nest due to the behavior-modifying effects of a behavior-modifying substance on said foraging ants such that said insecticide is distributed to other members of said population of ants and said ants are killed by exposure to said insecticide, said method comprising the step of:

providing to said foraging ants a bait comprising:
  (1) an insecticide comprising dodecachlorooctahydro-1,3,4-metheno-2H-cyclobuta pentalene;
  (2) a carrier for said insecticide which is transportable by said foraging ants from a location external to said ants' nest back to said population of ants; and
  (3) a behavior-modifying substance for said foraging ants comprising a mixture of 3-octanol and 3-octanone, said behavior-modifying substance being in association with said insecticide.

3. A method of controlling a population of a selected species of ants by inducing foraging members of said population of said selected species of ants to transport a toxic substance back to their nest due to the behavior-modifying effects of a behavior-modifying substance on said selected species of foraging ants such that said toxic substance is distributed to other members of said population of said selected species of ants and said selected species of ants are killed by exposure to said toxicant substance, said method comprising the step of:

providing to said selected species of foraging ants a bait consisting essentially of:
  (1) a toxic amount of a substance which is toxic to said selected species of ants which is transportable by said selected species of foraging ants from a location external to said ant's nest back to said population of said selected species of ants, said substance having delayed action sufficient to permit said selected species of foraging ants to transport said substance back to their nest before said selected species of foraging ants are killed by said substance;
  (2) an effective amount of a behavior-modifying substance selected from the group consisting of 3-octanol, 3-octanone, nonanol, decanal, dodecanal, 2-phenylethanol, citral, farnesol, 6-methyl-5-hepten-2-one, 4-methyl-3-heptanone, decanoic acid, geraniol, tetradecanal, β-pinene and mixtures thereof, said behavior modifying substance and said toxic substance being in association with each other; and whereby exposure of said selected species of ants to said behavior-modifying substance induces said selected species of ants to transport a greater amount of said toxic substance back to their nest, to admit said toxic substance to the nest and to distribute said toxic substance to other members of said population of said selected species of ants and said selected species of ants are killed by exposure to said toxic substance.

4. The method of claim 3, wherein said toxic substance is an insecticide.

5. The method of claim 3, wherein said toxic substance is a fungicide for a symbiotic fungus of said selected species of ants.

6. The method of claim 3, wherein said toxic substance comprises dodecachlorooctahydro-1,3,4-metheno-2H-cyclobuta pentalene.

7. The method of claim 3, wherein said toxic substance comprises a compound selected from the group consisting of pentachloronitrobenzene and Benomyl.

8. The method of claim 3, wherein said bait further comprises a food for said selected species of ants.

9. The method of claim 3, wherein said toxic substance and said behavior-modifying substance are contained in a sealed plastic film.

10. The method of claim 3, wherein said toxic substance and said behavior-modifying substance are contained in an openable sachet.

11. The method of claim 3, wherein said behavior modifying substance is in a slow-release form.

12. A method of improving the amount of toxic substance retrieval by a selected species of ants comprising the step of:

providing to foraging members of said selected species of ants a toxic substance in association with an effective amount of a behavior modifying substance, said behavior-modifying substance comprising the structural equivalent of at least one component of the alarm pheromone of said selected species of ants, whereby a greater amount of said toxic substance is retrieved by said selected species of ants.

* * * * *